United States Patent [19]

Roush

[11] Patent Number: 4,621,078

[45] Date of Patent: Nov. 4, 1986

[54] PESTICIDAL VINYL PHOSPHORIC ESTERS

[75] Inventor: David M. Roush, Princeton, N.J.

[73] Assignee: FMC Corporation, Philadelphia, Pa.

[21] Appl. No.: 709,483

[22] Filed: Mar. 7, 1985

[51] Int. Cl.$^4$ .......................... A01N 57/02; C07F 9/16
[52] U.S. Cl. ...................................... 514/127; 558/184
[58] Field of Search ...................... 260/948; 514/127; 558/184

[56] References Cited

U.S. PATENT DOCUMENTS

| | | | |
|---|---|---|---|
| 2,864,740 | 12/1958 | Diveley | 260/948 |
| 2,954,320 | 9/1960 | Gilbert et al. | 260/948 |

FOREIGN PATENT DOCUMENTS 1020809 2/1966 United Kingdom .

OTHER PUBLICATIONS

Bartlett et al., *J. Am. Chem. Soc.*, 100, 4852 (1978).
*Chem. Abstr.*, 90, 137463f (1979).
*Tet. Letters*, 22, 1287 (1981).
Unvarified Translation of Japan No. 52-93717, 6/1977.

Primary Examiner—Anton H. Sutto
Attorney, Agent, or Firm—R. L. Hansen; H. R. Ertelt

[57] ABSTRACT

Vinyl phosphoric esters of the following formula are effective in the control of insects and acarids:

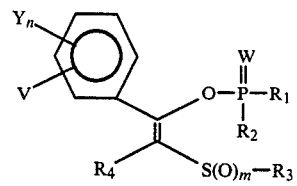

wherein
$R_1$ is lower alkoxy;
$R_2$ is selected from lower alkoxy and lower thioalkyl;
$R_3$ is selected from lower alkyl, phenyl, and halophenyl;
$R_4$ is selected from hydrogen, lower alkyl, halogen, and lower thioalkyl;
V is selected from hydrogen, halogen, lower alkyl, lower alkoxy, lower haloalkyl, amino, mono and dialkyl substituted amino, lower alkoxy carbonyl, lower thioalkyl, lower alkyl sulfonyl, nitro, and phenyl;
W is oxygen or sulfur;
Y is halogen;
m is 0-2; and
n is 0-2.

27 Claims, No Drawings

PESTICIDAL VINYL PHOSPHORIC ESTERS

This invention relates to novel organic compounds which are vinyl phosphoric esters, agricultural compositions containing the esters, and the method of using the compositions to control insects and acarids.

Compounds within the scope of this invention are represented by the following structural formula:

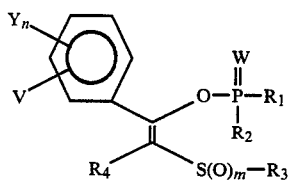

wherein
$R_1$ is lower alkoxy;
$R_2$ is selected from lower alkoxy and lower thioalkyl;
$R_3$ is selected from lower alkyl, phenyl, and halophenyl;
$R_4$ is selected from hydrogen, lower alkyl, halogen, and lower thioalkyl;
V is selected from hydrogen, halogen, lower alkyl, lower alkoxy, lower haloalkyl, amino, mono and dialkyl substituted amino, lower alkoxy carbonyl, lower thioalkyl, lower alkyl sulfonyl, nitro, and phenyl;
W is oxygen on sulfur;
Y is halogen;
m is 0–2; and
n is 0–2.

In the aforesaid description and whenever employed in this application the term "halogen" or "halo" means fluorine, chlorine and bromine. Similarly, the term "lower alkyl" means a straight or branched chain containing 1 to 6, preferably 1 to 4, carbon atoms, while "lower alkoxy" and "lower thioalkyl" contemplate bonded to oxygen and sulfur, respectively, a straight or branched chain containing 1 to 6, preferably 1 to 4, carbon atoms. The terms "haloalkyl," "halophenyl" or the like mean one or more hydrogen atoms has been replaced by halogen.

Still with reference to the aforesaid structural formula, preferred lower alkoxy substituents, e.g., $R_1$ and $R_2$, include methoxy and ethoxy. With regard to $R_3$, the lower alkyl compounds are generally the most active, and hydrogen is preferred as $R_4$.

In general, the phosphorothioates, in which W is sulfur, are more attractive than the phosphate counterparts. Substituent Y, when present, is preferably chlorine, and it is further preferred that V be a 2-substituent selected from halogen (especially chlorine), lower alkyl, lower haloalkyl, lower alkoxy carbonyl, or lower alkyl sulfonyl.

Specific compounds of interest include O-[1-(2,4-dichlorophenyl)-2-methylthioethenyl]O,O-diethyl phosphorothioate; O-[1-(2,4-dichlorophenyl)-2-methylsulfinylethenyl]O,O-diethyl phosphorothioate; and O-[1-(2,4-dichlorophenyl)-2-methylsulfonylethenyl]O,O-diethyl phosphorothioate.

The vinyl compounds of this invention are capable of existing as one, the other, or a mixture of both geometric isomers. In general, both isomers are active pesticides, but the level of activity often depends upon the specific isomer employed. When referred to hereinafter, the geometric isomers are named according to the E-Z nomenclature scheme; see Allinger, et al., "Organic Chemistry," Worth Publishers, Inc., New York, NY, 1971, p. 142.

The vinyl phosphoric esters of this invention are prepared by techniques known in the art. For example, an enol salt of an appropriately substituted thioacetophenone can be condensed with a chlorophosphate, chlorothiophosphate, or chlorodithiophosphate as described in Japanese Kokai No. 52-93717 or *J. Am. Chem. Soc.*, 100, 4852 (1978). Examples 28 and 52 below illustrate the method.

In general, a 2-thio-1-ethenyl ester, in which m is 0, can be oxidized stepwise to the corresponding 2-sulfinyl and 2-sulfonyl compounds in which m is 1 and 2, respectively. Such oxidation is described, for example, in *Tet. Letters*, 22, 1289 (1981) and in Example 54 below.

The preparation of compounds in which $R_4$ is other than hydrogen is illustrated in Example 109 below.

Synthesis of the vinyl phosphoric esters often leads to a mixture of the E and Z geometric isomers. Such mixtures generally can be separated into the component isomers by column chromatography using silica gel as the stationary phase and a mixture of hexane and ethyl acetate as the eluent. For identification purposes, the E and Z isomers can usually be distinguished based on the observation that the chemical shift ($\delta$) for the vinyl proton of the E isomer appears at 6.4–6.9 ppm, but at 5.9–6.5 ppm for the Z isomer.

EXAMPLE 28

O-[1-(2-Chlorophenyl)-2-Methylsulfonylethenyl]O,O-Diethyl Phosphorothioate

In a manner similar to that of *J. Am. Chem. Soc.*, 100, 4852 (1978), the reaction of 2-methylsulfonyl-1-(2-chlorophenyl)ethanone (2.4 g, 0.01 mole), diethyl chlorothiophosphate (2.28 g, 0.012 mole), and triethylamine (1.8 g, 0.018 mole) in 10.2 ml of acetonitrile produced 3.5 g of O-E,Z-[1-(2-chlorophenyl)-2-methylsulfonylethenyl]O-O-diethyl phosphorothioate as an oil, E/Z=75/25.

Analysis: Calc. for $C_{13}H_{18}ClO_5PS_2$: C, 40.57; H, 4.71; Found: C, 39.62; H, 4.97. nmr ($\delta$, $CDCl_3$): 1.32(t, 6H); 2.93(s, 3H, E isomer); 3.30(s, 3H, Z isomer); 4.22(dq, 4H); 6.20(s, 1H, Z isomer); 6.78(d, 1H, E isomer); 7.30–7.60(m, 4H).

EXAMPLE 52

O-[1-(2,4-Dichlorophenyl)-2-Methylthioethenyl]O-O-Diethyl Phosphorothioate

In a manner similar to that described in Japanese Kokai 52-93717, Example 2, the reaction of 1-(2,4-dichlorophenyl)-2-methylthioethanone (3.2 g, 0.014 mole) with sodium hydride (0.79 g, 0.016 mole) in approximately 65 ml of tetrahydrofuran produced the corresponding sodium salt. Further reaction with diethyl chlorothiophosphate (2.8 g, 0.014 mole) dissolved in a small amount of tetrahydrofuran produced an oil. Purification of this oil by column chromatography on silica gel, eluted with n-hexane: ethyl acetate (90:10), produced 1.1 g of O-Z-[1-(2,4-dichlorophenyl)-2-methylthioethenyl]O,O-diethyl phosphorothioate as an oil.

Analysis: Calc. for $C_{13}H_{17}Cl_2O_3PS_2$: C, 40.31; H, 4.43; Found: C, 39.30; H, 4.65. nmr ($\delta$, $CDCl_3$): 1.23 (t, 6H); 2.40 (s, 3H); 4.22 (dq, 4H); 6.07 (d, 1H); 7.20–7.50 (m, 3H).

EXAMPLE 54

O-[1-(2,4-Dichlorophenyl)-2-Methylsulfinylethenyl-]O,O-Diethyl Phosphorothioate

To a stirred, ice cold solution of O-Z-[1-(2,4-dichlorophenyl)-2-methylthioethenyl]O,O-diethyl phosphorothioate (1.5 g, 0.004 mole) in 50 ml of methylene chloride was added dropwise a solution of 3-chloroperoxybenzoic acid (0.9 g of 75%, 0.004 mole) in methylene chloride. After complete addition the reaction mixture was stirred at room temperature for one hour. This mixture was poured slowly into an aqueous 15% sodium hydroxide solution. The resultant mixture was extracted with methylene chloride. The extract was washed in succession with an aqueous 15% sodium hydroxide solution, water, and a saturated aqueous sodium chloride solution. The washed extract was dried over anhydrous magnesium sulfate and filtered. The filtrate was evaporated under reduced pressure to yield 0.85 g of O-Z-[1-(2,4-dichlorophenyl)-2-methylsulfinylethenyl]O,O-diethyl phosphorothioate as an oil.

Analysis: Calc. for $C_{13}H_{17}Cl_2O_4PS_2$: C, 38.72; H, 4.25; Found: C, 37.63; H, 4.44. nmr ($\delta$, $CDCl_3$): 1.10(t, 3H); 1.33(t, 3H); 2.90(s, 3H); 3.80–4.40 (m, 4H); 6.33 (d, 1H); 7.30–7.60 (m, 3H).

EXAMPLE 109

O-[2-Chloro-1-(2-Chlorophenyl)-2-Methylsulfonyl)Ethenyl]O,O-Diethyl Phosphate

A stirred mixture of 1-(2-chlorophenyl)-2-methylsulfonylethanone (3.7 g, 0.016 mole) and N-chlorosuccinimide (5.0 g, 0.036 mole) in 20 ml of carbon tetrachloride and 10 ml of methylene chloride was heated until all reactants were in solution. This solution was allowed to cool to room temperature, and 0.2 ml of concentrated hydrochloric acid was added. The reaction flask was irradiated with a 100 watt incandescent lamp for two hours. The resultant mixture was filtered and the filtrate rinsed with methylene chloride. The filtrate was evaporated under reduced pressure to leave an oil. This oil was dissolved in a small amount of methylene chloride and the resultant solution was stirred with 80 ml of saturated aqueous sodium bisulfate for five minutes. This mixture was extracted with methylene chloride and the extract washed in succession with water, saturated aqueous sodium bicarbonate, and saturated aqueous sodium chloride. The washed extract was dried over anhydrous magnesium sulfate and filtered. The filtrate was evaporated under reduced pressure to yield 3.0 g of 1-(2-chlorophenyl)-2,2-dichloro-2-methylsulfonylethanone as a solid (mp 81°–82° C.).

In a manner similar to Example 2 of GB 1,020,809 the reaction of 1-(2-chlorophenyl)-2,2-dichloro-2-methylsulfonylethanone (3.0 g, 0.01 mole) with triethylphosphite (1.9 g, 0.012 mole) in 28 ml of toluene produced 1.9 g of O-E,Z-[2-chloro-1-(2-chlorophenyl)-2-methylsulfonylethenyl]O,O-diethyl phosphate as an oil, E/Z=90/10.

Analysis: Calc. for $C_{13}H_{17}Cl_2O_6PS$: C, 38.72; H, 4.25; Found: C, 39.80; H, 4.50. nmr ($\delta$, $CDCl_3$): 1.27(t, 6H); 3.07(s, 3H, E isomer); 3.30(s, 3H, Z isomer); 4.10(dq, 4H); 7.50 (bs, 4H).

Other vinyl phosphonic esters within the scope of this invention, prepared and analyzed by similar methods, are described in Table I.

In the normal use of the vinyl phosphoric esters of the present invention, the esters usually will not be employed free from admixture or dilution, but ordinarily will be used in a suitable formulated composition compatible with the method of application and comprising an insecticidally or acaricidally effective amount of vinyl phosphoric ester. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present vinyl phosphoric esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the vinyl phosphoric esters. The granule particles are relatively large, a diameter of about 400–2500 microns typically. The particles are either impregnated with the ester from solution or coated with the vinyl phosphoric ester, adhesive sometimes being employed. Granules generally contain 0.05–10%, preferably 0.5–5%, active ingredient as the insecticidally or acaricidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects or acarids contains 1 part of vinyl phosphoric ester, such as O-[1-(2,4-dichlorophenyl)-2-methylthioethenyl]O,O-diethyl phosphorothioate, and 99 parts of talc.

The vinyl phosphoric esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% ester, such as O-[1-(2,4-dichlorophenyl)-2-methylthioethenyl]O,O-diethyl phosphorothioate, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects or acarids contains 1.5 parts each of sodium lignosulfonate and sodium laurylsulfate as wetting agents, 25 parts of O-[1-(2,4-dichlorophenyl)-2-methylthioethenyl]O,O-diethylphosphorothiate, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the vinyl phosphoric ester with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal or acaricidal composition.

Other useful formulations include simple solutions of the active ingredient in a solvent in which it is completely soluble at the desired concentration, such as acetone or other organic solvents.

An insecticidally or acaricidally effective amount of vinyl phosphoric ester in an insecticidal or acaricidal composition diluted for application is normally in the range of about 0.001% to about 8% by weight. Many variations of spraying and dusting compositions known in the art may be used by substituting the esters of this invention into compositions known or apparent in the art.

The insecticidal or acaricidal compositions of this invention may be formulated with other active ingredients, including other insecticides, nematicides, acaricides, fungicides, plant growth regulators, fertilizers, etc. In using the compositions to control insects or acarids, it is only necessary that an insecticidally or acaricidally effective amount of vinyl phosphoric ester be applied to the locus where control is desired. Such locus may, e.g., be the insects or acarids themselves, plants upon which the insects or acarids feed, or the insect or acarid habitat. When the locus is soil, e.g., soil in which agricultural crops are or will be planted, the active compound may be applied to and optionally incorporated into the soil. For most applications, an insecticidally or acaricidally effective amount will be about 75 to 4000 g per hectare, preferably 150 g to 3000 g per hectare.

The insecticidal and acaricidal activity of the vinyl phosphoric esters whose preparation is described above was evaluated as follows:

The compounds were tested by foliar application at various concentrations in aqueous solutions containing 10% acetone and 0.25% octyl phenoxypolyethoxy ethanol. The evaluation utilized Mexican bean beetle (*Epilachna varivestis*), southern armyworm (*Spodoptera eridania*), pea aphid (*Acyrthosiphon pisum*), and two-spotted mite (*Tetranychus urticae*).

In the cases of Mexican bean beetle and southern armyworm, pinto bean plants were placed on a revolving turntable in a hood, and the test solutions were applied with a sprayer. The test solutions were applied to the upper and lower surfaces of the plant leaves to runoff. The plants were then allowed to dry and were severed at the base of the stem before being placed in cups. Ten individuals of the appropriate insect species were placed in each cup and the cup covered. Mortality was read 48 hours later.

Fava bean was substituted for pinto bean in the case of pea aphid, and the treated, potted plants were placed in cups infested with ten individuals, and covered. Mortality was read 48 hours later.

Evaluation against twospotted spider mite was carried out by placing infested leaf sections carrying about 75 mites on the test plants, then spraying the test plants with a solution of test compound, and reading the mortality 48 hours later.

A number of the vinyl phosphoric esters were also found to be active against southern corn rootworm larvae.

The results of the tests appear in Table II.

TABLE I

Exemplary Vinyl Phosphoric Esters

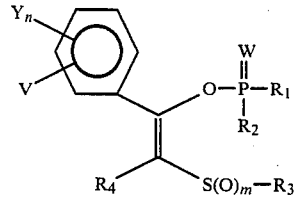

| Ex. | $R_1$ | $R_2$ | $R_3$ | $R_4$ | V | W | Y | m | n | E/Z |
|---|---|---|---|---|---|---|---|---|---|---|
| 1 | OEt | OEt | Me | H | H | S | | 0 | 0 | 0/100 |
| 2 | OEt | OEt | Et | H | H | S | | 0 | 0 | 0/100 |
| 3 | OEt | OEt | $C_6H_5$ | H | H | S | | 0 | 0 | 0/100 |
| 4 | OEt | OEt | $C_6H_5$ | H | H | S | | 0 | 0 | 70/30 |
| 5 | OEt | OEt | Me | H | H | S | | 1 | 0 | 0/100 |
| 6 | OEt | OEt | Et | H | H | S | | 1 | 0 | 0/100 |
| 7 | OEt | OEt | $C_6H_5$ | H | H | S | | 1 | 0 | 0/100 |
| 8 | OEt | OEt | Me | H | H | S | | 2 | 0 | 20/80 |
| 9 | OEt | OEt | $C_6H_5$ | H | H | S | | 2 | 0 | 67/33 |
| 10 | OEt | OEt | 4-$ClC_6H_4$ | H | H | S | | 2 | 0 | 40/60 |

TABLE I-continued
Exemplary Vinyl Phosphoric Esters

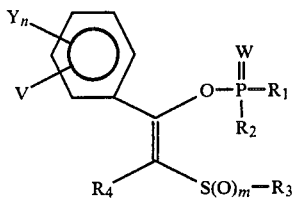

| Ex. | R₁ | R₂ | R₃ | R₄ | V | W | Y | m | n | E/Z |
|---|---|---|---|---|---|---|---|---|---|---|
| 11 | OEt | OEt | Me | H | 2-Cl | S | | 0 | 0 | 50/50 |
| 12 | OEt | OEt | iPr | H | 2-Cl | S | | 0 | 0 | 55/45 |
| 13 | OEt | OEt | C₆H₅ | H | 2-Cl | S | | 0 | 0 | 75/25 |
| 14 | OEt | OEt | 4-ClC₆H₄ | H | 2-Cl | S | | 0 | 0 | 75/25 |
| 15 | OEt | OEt | Me | H | 2-Me | S | | 0 | 0 | 50/50 |
| 16 | OEt | OEt | C₆H₅ | H | 2-Me | S | | 0 | 0 | 67/33 |
| 17 | OEt | OEt | 4-ClC₆H₄ | H | 2-Me | S | | 0 | 0 | 60/40 |
| 18 | OEt | OEt | Me | H | 4-Cl | S | | 0 | 0 | 0/100 |
| 19 | OEt | OEt | Me | H | 4-Me | S | | 0 | 0 | 0/100 |
| 20 | OEt | OEt | Me | H | 4-OMe | S | | 0 | 0 | 0/100 |
| 21 | OEt | OEt | Me | H | 4-NMe₂ | S | | 0 | 0 | 0/100 |
| 22 | OEt | OEt | Me | H | 4-Cl | S | | 1 | 0 | 0/100 |
| 23 | OEt | OEt | Me | H | 4-OMe | S | | 1 | 0 | 67/33 |
| 24 | OEt | OEt | Me | H | 2-F | S | | 2 | 0 | 100/0 |
| 25 | OEt | OEt | Me | H | 2-F | S | | 2 | 0 | 33/67 |
| 26 | OEt | OEt | Me | H | 2-Cl | S | | 2 | 0 | 100/0 |
| 27 | OEt | OEt | Me | H | 2-Cl | S | | 2 | 0 | 0/100 |
| 28 | OEt | OEt | Me | H | 2-Cl | S | | 2 | 0 | 75/25 |
| 29 | OEt | OEt | Me | H | 2-Br | S | | 2 | 0 | 55/45 |
| 30 | OEt | OEt | iPr | H | 2-Cl | S | | 2 | 0 | 75/25 |
| 31 | OEt | OEt | C₆H₅ | H | 2-Cl | S | | 2 | 0 | 80/20 |
| 32 | OEt | OEt | 4-ClC₆H₄ | H | 2-Cl | S | | 2 | 0 | 100/0 |
| 33 | OEt | OEt | Me | H | 2-Me | S | | 2 | 0 | 100/0 |
| 34 | OEt | OEt | Me | H | 2-Me | S | | 2 | 0 | 0/100 |
| 35 | OEt | OEt | C₆H₅ | H | 2-Me | S | | 2 | 0 | 90/10 |
| 36 | OEt | OEt | 4-ClC₆H₄ | H | 2-Me | S | | 2 | 0 | 85/15 |
| 37 | OEt | OEt | Me | H | 2-CF₃ | S | | 2 | 0 | 75/25 |
| 38 | OEt | OEt | Me | H | 2-COOMe | S | | 2 | 0 | 100/0 |
| 39 | OEt | OEt | Me | H | 2-COOMe | S | | 2 | 0 | 0/100 |
| 40 | OEt | OEt | Me | H | 2-OMe | S | | 2 | 0 | 0/100 |
| 41 | OEt | OEt | Me | H | 2-SMe | S | | 2 | 0 | 100/0 |
| 42 | OEt | OEt | Me | H | 2-SMe | S | | 2 | 0 | 0/100 |
| 43 | OEt | OEt | Me | H | 2-SO₂Me | S | | 2 | 0 | 100/0 |
| 44 | OEt | OEt | Me | H | 3-Br | S | | 2 | 0 | 0/100 |
| 45 | OEt | OEt | Me | H | 4-Cl | S | | 2 | 0 | 30/70 |
| 46 | OEt | OEt | Me | H | 4-Br | S | | 2 | 0 | 20/80 |
| 47 | OEt | OEt | Me | H | 4-Me | S | | 2 | 0 | 20/80 |
| 48 | OEt | OEt | Me | H | 4-NO₂ | S | | 2 | 0 | 0/100 |
| 49 | OEt | OEt | Me | H | 4-NO₂ | S | | 2 | 0 | 30/70 |
| 50 | OMe | OMe | Me | H | 3-CF₃ | S | | 2 | 0 | 100/0 |
| 51 | OMe | OMe | Me | H | 3-CF₃ | S | | 2 | 0 | 0/100 |
| 52 | OEt | OEt | Me | H | 2-Cl | S | 4-Cl | 0 | 1 | 0/100 |
| 53 | OEt | OEt | Me | H | 2-Cl | S | 4-Cl | 0 | 1 | 60/40 |
| 54 | OEt | OEt | Me | H | 2-Cl | S | 4-Cl | 1 | 1 | 0/100 |
| 55 | OEt | OEt | Me | H | 2-Cl | S | 4-Cl | 2 | 1 | 75/25 |
| 56 | OEt | OEt | C₆H₅ | H | 2-Cl | S | 4-Cl | 2 | 1 | 90/10 |
| 57 | OEt | OEt | Me | H | 2-Cl | S | 6-Cl | 2 | 1 | 100/0 |
| 58 | OEt | Ome | Me | H | 2-Cl | S | 4-Cl | 0 | 1 | 67/33 |
| 59 | OEt | OEt | Me | H | 2-Cl | S | 4,5(Cl)₂ | 0 | 2 | 0/100 |
| 60 | OEt | OEt | Me | H | 2-Cl | S | 4,5(Cl)₂ | 2 | 2 | 100/0 |
| 61 | OEt | OEt | Me | H | 2-Cl | S | 4,5(Cl)₂ | 2 | 2 | 70/30 |
| 62 | OEt | OEt | Me | Cl | H | S | | 0 | 0 | |
| 63 | OEt | OEt | Me | Cl | H | S | | 0 | 0 | |
| 64 | OEt | OEt | Me | Me | H | S | | 0 | 0 | 67/33 |
| 65 | OEt | OEt | Me | SMe | 2-Cl | S | | 0 | 0 | |
| 66 | OEt | OEt | Me | SMe | 2-Cl | S | 4-Cl | 0 | 1 | |
| 67 | OEt | OEt | Me | H | H | O | | 0 | 0 | 33/67 |
| 68 | OEt | OEt | C₆H₅ | H | H | O | | 0 | 0 | 0/100 |
| 69 | OEt | OEt | Me | H | H | O | | 1 | 0 | 33/67 |
| 70 | OEt | OEt | C₆H₅ | H | H | O | | 1 | 0 | 50/50 |
| 71 | OEt | OEt | Me | H | H | O | | 2 | 0 | 15/85 |
| 72 | OEt | OEt | C₆H₅ | H | H | O | | 2 | 0 | 0/100 |
| 73 | OEt | OEt | C₆H₅ | H | H | 0 | | 2 | 0 | 33/67 |
| 74 | OEt | OEt | 4-ClC₆H₄ | H | H | 0 | | 2 | 0 | 10/90 |
| 75 | OEt | OEt | iPr | H | 2-Cl | O | | 0 | 0 | 60/40 |
| 76 | OEt | OEt | Me | H | 4-Cl | O | | 0 | 0 | 0/100 |
| 77 | OEt | OEt | Me | H | 4-Br | O | | 0 | 0 | 0/100 |
| 78 | OEt | OEt | Me | H | 4-Me | O | | 0 | 0 | 0/100 |

TABLE I-continued

Exemplary Vinyl Phosphoric Esters

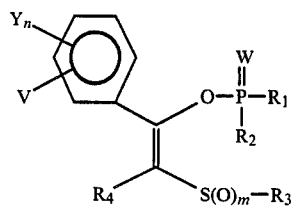

| Ex. | R₁ | R₂ | R₃ | R₄ | V | W | Y | m | n | E/Z |
|---|---|---|---|---|---|---|---|---|---|---|
| 79 | OEt | OEt | Me | H | 4-OMe | O | | 0 | 0 | 0/100 |
| 80 | OEt | OEt | Me | H | 4-C₆H₅ | O | | 0 | 0 | 0/100 |
| 81 | OEt | OEt | Me | H | 4-Cl | O | | 1 | 0 | 0/100 |
| 82 | OEt | OEt | Me | H | 4-Br | O | | 1 | 0 | 0/100 |
| 83 | OEt | OEt | Me | H | 4-Me | O | | 1 | 0 | 0/100 |
| 84 | OEt | OEt | Me | H | 4-OMe | O | | 1 | 0 | 0/100 |
| 85 | OEt | OEt | Me | H | 4-C₆H₅ | O | | 1 | 0 | 0/100 |
| 86 | OEt | OEt | C₆H₅ | H | 2-Cl | O | | 2 | 0 | 0/100 |
| 87 | OEt | OEt | 4-ClC₆H₄ | H | 2-Cl | O | | 2 | 0 | 20/80 |
| 88 | OEt | OEt | C₆H₅ | H | 2-Me | O | | 2 | 0 | 70/30 |
| 89 | OEt | OEt | Me | H | 2-COOMe | O | | 2 | 0 | 50/50 |
| 90 | OEt | OEt | Me | H | 2-SMe | O | | 2 | O | 20/80 |
| 91 | OEt | OEt | Me | H | 4-Cl | O | | 2 | 0 | 0/100 |
| 92 | OEt | OEt | Me | H | 4-Br | O | | 2 | 0 | 20/80 |
| 93 | OEt | OEt | Me | H | 4-Me | O | | 2 | 0 | 0/100 |
| 94 | OEt | OEt | Me | H | 4-OMe | O | | 2 | 0 | 0/100 |
| 95 | OEt | OEt | Me | H | 2-Cl | O | 4-Cl | 0 | 1 | 0/100 |
| 96 | OEt | OEt | Me | H | 2-Cl | O | 4-Cl | 1 | 1 | 0/100 |
| 97 | OEt | OEt | Me | H | 2-Cl | O | 4-Cl | 2 | 1 | 0/100 |
| 98 | OEt | OEt | C₆H₅ | H | 2-Cl | O | 4-Cl | 2 | 1 | 100/0 |
| 99 | OEt | OEt | C₆H₅ | H | 2-Cl | O | 4-Cl | 2 | 1 | 0/100 |
| 100 | OEt | OEt | C₆H₅ | H | 2-Cl | O | 4-Cl | 2 | 1 | 50/50 |
| 101 | OEt | OEt | Me | Cl | H | O | | 0 | 0 | |
| 102 | OEt | OEt | Et | Cl | H | O | | 0 | 0 | 50/50 |
| 103 | OEt | OEt | Me | Me | H | O | | 0 | 0 | 20/80 |
| 104 | OEt | OEt | Me | Cl | 4-Cl | O | | 0 | 0 | |
| 105 | OEt | OEt | Me | Cl | H | O | | 1 | 0 | |
| 106 | OEt | OEt | Me | Me | H | O | | 1 | 0 | 20/80 |
| 107 | OEt | OEt | Me | Cl | H | O | | 2 | 0 | |
| 108 | OEt | OEt | Me | Me | H | O | | 2 | 0 | 20/80 |
| 109 | OEt | OEt | Me | Cl | 2-Cl | O | | 2 | 0 | 90/10 |
| 110 | OEt | OEt | C₆H₅ | Cl | 2-Cl | O | | 2 | 0 | 30/70 |
| 111 | OEt | OEt | Me | Cl | 2-Me | O | | 2 | 0 | 100/0 |
| 112 | OEt | S(iBu) | Me | H | 2-Me | S | | 0 | 0 | 20/80 |
| 113 | OEt | S(iBu) | Me | H | 2-Me | S | | 2 | 0 | 100/0 |
| 114 | OEt | S(iBu) | Me | H | 2-Me | S | | 2 | 0 | 50/50 |
| 115 | OEt | S(iBu) | Me | H | 2-Cl | S | 4-Cl | 0 | 1 | 15/85 |

TABLE II

Efficacy of Vinyl Phosphoric Esters

| Ex. | Appl. Rate (ppm) | MBB | PA | SAW | TSM |
|---|---|---|---|---|---|
| 1 | 1250 | 40 | 80 | 0 | 100 |
| 2 | 1250 | 90 | 100 | 0 | 0 |
| 3 | 1250 | 0 | 0 | 0 | 90 |
| 4 | 1000 | 100 | 100 | 0 | 100 |
| 5 | 1250 | 20 | 80 | 0 | 100 |
| 6 | 1250 | 20 | 0 | 0 | 100 |
| 7 | 1250 | 90 | 50 | 0 | 100 |
| 8 | 1250 | | 100 | 0 | 100 |
|   | 64 | 0 | 100 | | 100 |
| 9 | 1250 | | 100 | 100 | 100 |
|   | 1200 | 95 | | 58 | |
| 10 | 1000 | 100 | | 80 | 100 |
| 11 | 1000 | 100 | 100 | 90 | 100 |
| 12 | 1000 | 100 | 100 | 25 | 100 |
| 13 | 1000 | 100 | 100 | 50 | 80 |
| 14 | 1000 | 100 | 100 | 45 | 100 |
| 15 | 1000 | 100 | 100 | 55 | 100 |
| 16 | 1000 | 80 | 100 | 100 | 100 |
| 17 | 1000 | 0 | 100 | 50 | 100 |
| 18 | 1250 | 100 | 95 | 20 | 100 |
| 19 | 1250 | 90 | 65 | 30 | 75 |
| 20 | 1250 | 0 | 0 | 0 | 100 |
| 21 | 1250 | 0 | 0 | 0 | 100 |
| 22 | 1250 | 65 | 0 | 0 | 100 |
| 23 | 1250 | 0 | 0 | 0 | 100 |
| 24 | 1000 | 100 | | 100 | 100 |
| 25 | 1000 | 100 | | 100 | 100 |
| 26 | 2000 | 100 | 100 | 95 | 100 |
| 27 | 2000 | 95 | 15 | | 100 |
|   | 600 | | | 45 | |
| 28 | 1250 | 100 | | 90 | 100 |
|   | 1200 | 100 | 100 | 95 | |
| 29 | 2000 | 100 | 100 | 100 | |
|   | 1250 | 0 | | 30 | 100 |
| 30 | 1000 | 100 | 100 | 80 | 100 |
| 31 | 1000 | 100 | 0 | 0 | 100 |
| 32 | 1000 | 70 | 100 | 100 | 100 |
| 33 | 1000 | 0 | | 80 | 100 |
| 34 | 1000 | 0 | | 0 | 100 |
| 35 | 1000 | 100 | 100 | 85 | 100 |
| 36 | 600 | 90 | 90 | 90 | |
|   | 150 | 60 | 15 | 25 | 100 |
| 37 | 1000 | 100 | 100 | 48 | 100 |
| 38 | 1000 | 100 | 100 | 50 | 100 |
| 39 | 1000 | 75 | 80 | 0 | 100 |
| 40 | 1250 | 0 | | 0 | 100 |

TABLE II-continued
Efficacy of Vinyl Phosphoric Esters

| Ex. | Appl. Rate (ppm) | MBB | PA | SAW | TSM |
|---|---|---|---|---|---|
| 41 | 1000 | 75 | 100 | 50 | 100 |
| 42 | 1000 | 65 | 0 | 0 | 0 |
| 43 | 1000 | 0 | 100 | 10 | 100 |
| 44 | 1000 | 0 | | 0 | 100 |
| 45 | 1250 | 0 | 0 | 0 | 100 |
| 46 | 1250 | 0 | 0 | 0 | 100 |
| 47 | 1250 | 0 | 95 | 0 | 100 |
| 48 | 1000 | 55 | | 0 | 100 |
| 49 | 1000 | 0 | | 0 | 100 |
| 50 | 1250 | 0 | | 0 | 100 |
| 51 | 1250 | 0 | 0 | 0 | |
| | 1200 | 20 | 20 | | |
| 52 | 1250 | 100 | 100 | 100 | 100 |
| 53 | 600 | 95 | 100 | 43 | 100 |
| 54 | 1250 | 40 | 100 | 100 | 100 |
| 55 | 1250 | 100 | 100 | 100 | 100 |
| 56 | 1000 | 100 | | 100 | 100 |
| 57 | 1000 | 95 | 0 | 100 | 100 |
| 58 | 1000 | 100 | 100 | 0 | 0 |
| 59 | 1000 | 100 | 100 | 100 | 100 |
| 60 | 100 | 80 | 60 | 90 | 100 |
| 61 | 1000 | 80 | 80 | 75 | 100 |
| 62 | 1250 | 55 | 90 | 100 | 100 |
| 63 | 1250 | 80 | 100 | 0 | 100 |
| 64 | 1250 | 0 | 100 | 0 | 100 |
| 65 | 1000 | 90 | 100 | 95 | 100 |
| 66 | 1000 | 100 | 0 | 65 | 100 |
| 67 | 1250 | 100 | 100 | 0 | 100 |
| 68 | 1250 | 100 | 25 | 0 | 100 |
| 69 | 1250 | 100 | 100 | 70 | 100 |
| 70 | 1250 | 60 | 100 | 0 | 100 |
| 71 | 1250 | 100 | 50 | 0 | 100 |
| 72 | 1250 | 40 | 0 | 0 | 90 |
| 73 | 64 | 68 | 50 | 25 | 62 |
| 74 | 1000 | 40 | 0 | 0 | 100 |
| 75 | 1000 | 100 | 100 | 25 | 100 |
| 76 | 1250 | 100 | 95 | 0 | 100 |
| 77 | 1250 | 85 | 100 | 0 | 100 |
| 78 | 1250 | 40 | 70 | 0 | 100 |
| 79 | 1250 | 30 | 100 | 0 | 100 |
| 80 | 1250 | 80 | 60 | 0 | 85 |
| 81 | 1250 | 75 | 20 | 0 | 100 |
| 82 | 1250 | 100 | 100 | 0 | 70 |
| 83 | 1250 | 0 | 0 | 0 | 100 |
| 84 | 1250 | 35 | 100 | 0 | 0 |
| 85 | 1250 | 0 | 0 | 0 | 95 |
| 86 | 1000 | 70 | 30 | 0 | 100 |
| 87 | 1000 | 35 | 0 | 0 | 100 |
| 88 | 1000 | 100 | 100 | 0 | 0 |
| 89 | 1000 | 95 | 100 | 0 | 100 |
| 90 | 1000 | 0 | 100 | 0 | 100 |
| 91 | 1250 | 95 | 0 | 0 | 90 |
| 92 | 1250 | 90 | 100 | 0 | 100 |
| 93 | 1250 | 0 | 0 | 0 | 100 |
| 94 | 1250 | 50 | 100 | 0 | 0 |
| 95 | 1250 | 100 | 100 | 70 | 100 |
| 96 | 1250 | 100 | 85 | 0 | 100 |
| 97 | 1250 | 100 | 100 | 35 | 100 |
| 98 | 1000 | 95 | 0 | 0 | 100 |
| 99 | 1000 | 60 | 0 | 0 | 100 |
| 100 | 1000 | 25 | | 0 | 0 |
| 101 | 1250 | | 100 | 0 | 100 |
| 102 | 1250 | 0 | 0 | 0 | 65 |
| 103 | 1250 | 40 | 100 | 0 | 100 |
| 104 | 1250 | 100 | 100 | 100 | 100 |
| 105 | 1250 | 100 | 100 | 80 | 100 |
| 106 | 1250 | 50 | 80 | 0 | 0 |
| 107 | 1250 | 100 | 100 | 30 | 100 |
| 108 | 1250 | 100 | 90 | 20 | 80 |
| 109 | 1000 | 100 | 100 | 30 | 100 |
| 110 | 1000 | 55 | 3 | 3 | 100 |
| 111 | 1000 | 0 | 0 | 0 | 100 |
| 112 | 1000 | 100 | 100 | 100 | 100 |
| 113 | 1000 | 100 | 100 | 100 | 100 |
| 114 | 1000 | 100 | 100 | 100 | 100 |
| 115 | 1000 | 100 | 0 | 100 | 100 |

[a] MBB = Mexican bean beetle
PA = Pea aphid
SAW = Southern armyworm
TSM = Twospotted spider mite

What is claimed is:

1. The method of controlling insects or acarides which comprises applying to the locus where control is desired an insecticidally or acaricidally effective amount of at least one vinyl phosphoric ester of the formula $$\begin{array}{c} Y_n\text{—}\bigcirc\text{—}C(R_4)=C(S(O)_m\text{—}R_3)\text{—}O\text{—}P(=S)(R_1)(R_2) \\ V \end{array}$$

wherein
$R_1$ is lower alkoxy;
$R_2$ is selected from lower alkoxy and lower thioalkyl;
$R_3$ is selected from lower alkyl, phenyl, and halophenyl;
$R_4$ is selected from hydrogen, halogen, and lower thioalkyl;
V is selected from halogen, lower alkyl, lower haloalkyl, lower alkoxy carbonyl, and lower alkyl sulfonyl;
Y is halogen;
m is 0–2, provided m is not 0 when V is lower alkyl; and
n is 0–2.

2. The method of claim 1 wherein $R_1$ and $R_2$ are selected from methoxy and ethoxy.

3. The method of claim 1 wherein $R_3$ is lower alkyl.

4. The method of claim 1 wherein $R_4$ is hydrogen.

5. The method of claim 1 wherein Y is chlorine.

6. The method of claim 1 wherein V is chlorine.

7. The method of claim 1 wherein said vinyl phosphoric ester is O-[1-(2,4-dichlorophenyl)-2-methylthioethenyl]O,O-diethylphosphorothioate.

8. The method of claim 1 wherein said vinyl phosphoric ester is O-[1-(2,4-dichlorophenyl)-2-methylsulfinylethenyl]O,O-diethylphosphorothioate.

9. The method of claim 1 wherein said vinyl phosphoric ester is O-[1-(2,4-dichlorophenyl)-2-methylsulfonylethenyl]O,O-diethylphosphorothioate.

10. Pesticidal vinyl phosphoric esters of the formula $$\begin{array}{c} Y_n\text{—}\bigcirc\text{—}C(R_4)=C(S(O)_m\text{—}R_3)\text{—}O\text{—}P(=S)(R_1)(R_2) \\ V \end{array}$$

wherein
$R_1$ is lower alkoxy;
$R_2$ is selected from lower alkoxy and lower thioalkyl;

$R_3$ is selected from lower alkyl, phenyl, and halophenyl;

$R_4$ is selected from hydrogen, halogen, and lower thioalkyl;

V is selected from halogen, lower alkyl, lower haloalkyl, lower alkoxy carbonyl, and lower alkyl sulfonyl;

Y is halogen;

m is 0–2, provided m is not 0 when V is lower alkyl; and n is 0–2.

11. Esters of claim 10 wherein $R_1$ and $R_2$ are selected from methoxy and ethoxy.

12. Esters of claim 10 wherein $R_3$ is lower alkyl.

13. Esters of claim 10 wherein $R_4$ is hydrogen.

14. Esters of claim 10 wherein Y is chlorine.

15. Esters of claim 10 wherein V is chlorine.

16. O-[1-(2,4-dichlorophenyl)-2-methylthioethenyl]O,O-diethylphosphorothioate.

17. O-[1-(2,4-dichlorophenyl)-2-methylsulfinylethenyl]O,O-diethylphosphorothioate.

18. O-[1-(2,4-dichlorophenyl)-2-methylsulfonylethenyl]O,O-diethylphosphorothioate.

19. Insecticidal or acaricidal compositions comprising in admixture with an agriculturally acceptable carrier an insecticidally or acaricidally effective amount of at least one vinyl phosphoric ester of the formula

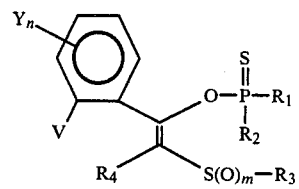

wherein $R_1$ is lower alkoxy;

$R_2$ is selected from lower alkoxy and lower thioalkyl;

$R_3$ is selected from lower alkyl, phenyl, and halophenyl;

$R_4$ is selected from hydrogen, halogen, and lower thioalkyl;

V is selected from halogen, lower alkyl, lower haloalkyl, lower alkoxy carbonyl, and lower alkyl sulfonyl;

Y is halogen;

m is 0–2, provided m is not 0 when V is lower alkyl; and n is 0–2.

20. Compositions of claim 19 wherein $R_1$ and $R_2$ are selected from methoxy and ethoxy.

21. Compositions of claim 19 wherein $R_3$ is lower alkyl.

22. Compositions of claim 19 wherein $R_4$ is hydrogen.

23. Compositions of claim 19 wherein Y is chlorine.

24. Compositions of claim 19 wherein V is chlorine.

25. Compositions of claim 19 wherein said vinyl phosphoric ester is O-[1-(2,4-dichlorophenyl-2-methylthioethenyl]O,O-diethylphosphorothioate.

26. Compositions of claim 19 wherein said vinyl phosphoric ester is O-[1-(2,4-dichlorophenyl)-2-methylsulfinylethenyl]O,O-diethylphosphorothioate.

27. Compositions of claim 19 wherein said vinyl phosphoric ester is O-[1-(2,4-dichlorophenyl)-2-methylsulfonylethenyl]O,O-diethylphosphorothioate.

* * * * *